(12) United States Patent
Boesen et al.

(10) Patent No.: US 10,342,428 B2
(45) Date of Patent: Jul. 9, 2019

(54) MONITORING PULSE TRANSMISSIONS USING RADAR

(71) Applicant: BRAGI GmbH, München (DE)

(72) Inventors: Peter Vincent Boesen, München (DE); Nikolaj Hviid, München (DE)

(73) Assignee: BRAGI GmbH, München (DE)

( * ) Notice: Subject to any disclaimer, the term of this patent is extended or adjusted under 35 U.S.C. 154(b) by 0 days.

(21) Appl. No.: 15/347,763

(22) Filed: Nov. 9, 2016

(65) Prior Publication Data

US 2017/0105622 A1 Apr. 20, 2017

Related U.S. Application Data

(63) Continuation of application No. 15/290,459, filed on Oct. 11, 2016.

(Continued)

(51) Int. Cl.
*A61B 5/00* (2006.01)
*G06F 1/16* (2006.01)
(Continued)

(52) U.S. Cl.
CPC .......... *A61B 5/0024* (2013.01); *A61B 5/0245* (2013.01); *A61B 5/02416* (2013.01);
(Continued)

(58) Field of Classification Search
CPC . A61B 5/0024; A61B 5/02416; A61B 5/0245; A61B 5/6803; A61B 5/742; G02B 27/0172; G02B 2027/014; G02B 2027/0178; G06F 1/163; G06F 3/03547; G06F 3/0488; G06F 21/32; G06F 21/35; G06F 2221/2153; H04L 63/0861; H04W 12/06; H04W 76/023; H04W 4/008; H04R 1/1016; H04R 1/1041; H04R 1/1083; H04R 25/43; H04R 25/552; H04R 2225/31; H04R 2420/07; H04R 2430/01; H04R 2460/13
(Continued)

(56) References Cited

U.S. PATENT DOCUMENTS 3,934,100 A 1/1976 Harada
4,150,262 A 4/1979 Ono
(Continued)

FOREIGN PATENT DOCUMENTS

EP 1017252 A2 7/2000
GB 2074817 4/1981
(Continued)

OTHER PUBLICATIONS

Announcing the $3,333,333 Stretch Goal (Feb. 24, 2014).
(Continued)

*Primary Examiner* — Sean H Nguyen
(74) *Attorney, Agent, or Firm* — Goodhue, Coleman & Owens, P.C.

(57) ABSTRACT

A method for improving biometric data by using a plurality of wearable devices on a network includes making a first measurement at a first wearable sensor at a first location on a body, making a second measurement at a second wearable sensor positioned at a second location on the body, and detecting an arterial pulse wave transmit time using the first measurement and the second measurement.

9 Claims, 5 Drawing Sheets

Related U.S. Application Data

(60) Provisional application No. 62/244,147, filed on Oct. 20, 2015.

(51) Int. Cl.

| | | |
|---|---|---|
| *H04R 1/10* | (2006.01) | |
| *H04W 4/80* | (2018.01) | |
| *A61B 5/024* | (2006.01) | |
| *G02B 27/01* | (2006.01) | |
| *G06F 21/32* | (2013.01) | |
| *G06F 21/35* | (2013.01) | |
| *H04L 29/06* | (2006.01) | |
| *H04R 25/00* | (2006.01) | |
| *H04W 12/06* | (2009.01) | |
| *H04W 76/14* | (2018.01) | |
| *A61B 5/0245* | (2006.01) | |
| *G06F 3/0354* | (2013.01) | |
| *G06F 3/0488* | (2013.01) | |

(52) U.S. Cl.
CPC ........ *A61B 5/02438* (2013.01); *A61B 5/6803* (2013.01); *A61B 5/742* (2013.01); *G02B 27/0172* (2013.01); *G06F 1/163* (2013.01); *G06F 3/03547* (2013.01); *G06F 3/0488* (2013.01); *G06F 21/32* (2013.01); *G06F 21/35* (2013.01); *H04L 63/0861* (2013.01); *H04W 12/06* (2013.01); *H04W 76/14* (2018.02); *G02B 2027/014* (2013.01); *G02B 2027/0178* (2013.01); *G06F 2221/2153* (2013.01); *H04R 1/1016* (2013.01); *H04R 1/1041* (2013.01); *H04R 1/1083* (2013.01); *H04R 25/43* (2013.01); *H04R 25/552* (2013.01); *H04R 2225/31* (2013.01); *H04R 2420/07* (2013.01); *H04R 2430/01* (2013.01); *H04R 2460/13* (2013.01); *H04W 4/80* (2018.02)

(58) Field of Classification Search
USPC ........................................................ 381/370
See application file for complete search history.

(56) References Cited

U.S. PATENT DOCUMENTS

| | | |
|---|---|---|
| 4,334,315 A | 6/1982 | Ono et al. |
| 4,375,016 A | 2/1983 | Harada |
| 4,588,867 A | 5/1986 | Konomi |
| 4,654,883 A | 3/1987 | Iwata |
| 4,682,180 A | 7/1987 | Gans |
| 4,791,673 A | 12/1988 | Schreiber |
| 4,865,044 A | 9/1989 | Wallace et al. |
| 5,191,602 A | 3/1993 | Regen et al. |
| 5,201,007 A | 4/1993 | Ward et al. |
| 5,280,524 A | 1/1994 | Norris |
| 5,295,193 A | 3/1994 | Ono |
| 5,298,692 A | 3/1994 | Ikeda et al. |
| 5,343,532 A | 8/1994 | Shugart |
| 5,363,444 A | 11/1994 | Norris |
| 5,497,339 A | 3/1996 | Bernard |
| 5,606,621 A | 2/1997 | Reiter et al. |
| 5,613,222 A | 3/1997 | Guenther |
| 5,692,059 A | 11/1997 | Kruger |
| 5,721,783 A | 2/1998 | Anderson |
| 5,749,072 A | 5/1998 | Mazurkiewicz et al. |
| 5,771,438 A | 6/1998 | Palermo et al. |
| 5,802,167 A | 9/1998 | Hong |
| 5,929,774 A | 7/1999 | Charlton |
| 5,933,506 A | 8/1999 | Aoki et al. |
| 5,949,896 A | 9/1999 | Nageno et al. |
| 5,987,146 A | 11/1999 | Pluvinage et al. |
| 6,021,207 A | 2/2000 | Puthuff et al. |
| 6,054,989 A | 4/2000 | Robertson et al. |
| 6,081,724 A | 6/2000 | Wilson |
| 6,094,492 A | 7/2000 | Boesen |
| 6,111,569 A | 8/2000 | Brusky et al. |
| 6,112,103 A | 8/2000 | Puthuff |
| 6,157,727 A | 12/2000 | Rueda |
| 6,167,039 A | 12/2000 | Karlsson et al. |
| 6,181,801 B1 | 1/2001 | Puthuff et al. |
| 6,208,372 B1 | 3/2001 | Barraclough |
| 6,230,029 B1 | 5/2001 | Yegiazaryan et al. |
| 6,275,789 B1 | 8/2001 | Moser et al. |
| 6,339,706 B1 | 1/2002 | Tillgren et al. |
| 6,339,754 B1 | 1/2002 | Flanagan et al. |
| 6,408,081 B1 | 6/2002 | Boesen |
| 6,424,820 B1 | 7/2002 | Burdick et al. |
| D464,039 S | 10/2002 | Boesen |
| 6,470,893 B1 | 10/2002 | Boesen |
| D468,299 S | 1/2003 | Boesen |
| D468,300 S | 1/2003 | Boesen |
| 6,542,721 B2 | 4/2003 | Boesen |
| 6,560,468 B1 | 5/2003 | Boesen |
| 6,654,721 B2 | 11/2003 | Handelman |
| 6,664,713 B2 | 12/2003 | Boesen |
| 6,694,180 B1 | 2/2004 | Boesen |
| 6,718,043 B1 | 4/2004 | Boesen |
| 6,738,485 B1 | 5/2004 | Boesen |
| 6,748,095 B1 | 6/2004 | Goss |
| 6,754,358 B1 | 6/2004 | Boesen et al. |
| 6,784,873 B1 | 8/2004 | Boesen et al. |
| 6,823,195 B1 | 11/2004 | Boesen |
| 6,852,084 B1 | 2/2005 | Boesen |
| 6,879,698 B2 | 4/2005 | Boesen |
| 6,892,082 B2 | 5/2005 | Boesen |
| 6,920,229 B2 | 7/2005 | Boesen |
| 6,952,483 B2 | 10/2005 | Boesen et al. |
| 6,987,986 B2 | 1/2006 | Boesen |
| 7,136,282 B1 | 11/2006 | Rebeske |
| 7,203,331 B2 | 4/2007 | Boesen |
| 7,209,569 B2 | 4/2007 | Boesen |
| 7,215,790 B2 | 5/2007 | Boesen et al. |
| 7,463,902 B2 | 12/2008 | Boesen |
| 7,508,411 B2 | 3/2009 | Boesen |
| 7,979,035 B2 | 7/2011 | Griffin et al. |
| 7,983,628 B2 | 7/2011 | Boesen |
| 8,095,188 B2 | 1/2012 | Shi |
| 8,140,357 B1 | 3/2012 | Boesen |
| 8,300,864 B2 | 10/2012 | Mullenborn et al. |
| 8,436,780 B2 | 5/2013 | Schantz et al. |
| 8,719,877 B2 | 5/2014 | VonDoenhoff et al. |
| 2001/0005197 A1 | 6/2001 | Mishra et al. |
| 2001/0027121 A1 | 10/2001 | Boesen |
| 2001/0056350 A1 | 12/2001 | Calderone et al. |
| 2002/0002413 A1 | 1/2002 | Tokue |
| 2002/0007510 A1 | 1/2002 | Mann |
| 2002/0010590 A1 | 1/2002 | Lee |
| 2002/0030637 A1 | 3/2002 | Mann |
| 2002/0046035 A1 | 4/2002 | Kitahara et al. |
| 2002/0057810 A1 | 5/2002 | Boesen |
| 2002/0076073 A1 | 6/2002 | Taenzer et al. |
| 2002/0118852 A1 | 8/2002 | Boesen |
| 2003/0065504 A1 | 4/2003 | Kraemer et al. |
| 2003/0100331 A1 | 5/2003 | Dress et al. |
| 2003/0104806 A1 | 6/2003 | Ruef et al. |
| 2003/0115068 A1 | 6/2003 | Boesen |
| 2003/0125096 A1 | 7/2003 | Boesen |
| 2003/0218064 A1 | 11/2003 | Conner et al. |
| 2004/0070564 A1 | 4/2004 | Dawson et al. |
| 2004/0160511 A1 | 8/2004 | Boesen |
| 2005/0043056 A1 | 2/2005 | Boesen |
| 2005/0125320 A1 | 6/2005 | Boesen |
| 2005/0148883 A1 | 7/2005 | Boesen |
| 2005/0165663 A1 | 7/2005 | Razumov |
| 2005/0196009 A1 | 9/2005 | Boesen |
| 2005/0251455 A1 | 11/2005 | Boesen |
| 2005/0266876 A1 | 12/2005 | Boesen |
| 2006/0029246 A1 | 2/2006 | Boesen |
| 2006/0074671 A1 | 4/2006 | Farmaner et al. |
| 2006/0074808 A1 | 4/2006 | Boesen |
| 2008/0254780 A1 | 10/2008 | Kuhl et al. |

(56) References Cited

U.S. PATENT DOCUMENTS

| | | | |
|---|---|---|---|
| 2009/0073070 A1 | 3/2009 | Rofougaran | |
| 2010/0172522 A1 | 7/2010 | Mooring et al. | |
| 2010/0203831 A1 | 8/2010 | Muth | |
| 2013/0176202 A1 | 7/2013 | Gervautz | |
| 2014/0254024 A1 | 9/2014 | Hiraide et al. | |
| 2015/0131814 A1 | 5/2015 | Usher et al. | |
| 2015/0208945 A1* | 7/2015 | Lux | A61B 5/0507 600/430 |
| 2015/0234187 A1 | 8/2015 | Lee | |
| 2015/0264474 A1 | 9/2015 | Seo et al. | |
| 2016/0107591 A1 | 4/2016 | Heo | |
| 2016/0154493 A1 | 6/2016 | Song | |
| 2016/0191511 A1* | 6/2016 | Tijerina | H04L 63/0853 726/7 |
| 2017/0086739 A1* | 3/2017 | Masuda | A61B 5/7278 |
| 2017/0108697 A1 | 4/2017 | El-Ghoroury et al. | |
| 2017/0258329 A1* | 9/2017 | Marsh | A61B 5/0024 |

FOREIGN PATENT DOCUMENTS

| | | |
|---|---|---|
| JP | 06292195 | 10/1998 |
| WO | 2014043179 A2 | 3/2014 |
| WO | 2015110577 A1 | 7/2015 |
| WO | 2015110587 A1 | 7/2015 |

OTHER PUBLICATIONS

BRAGI Is on Facebook (2014).
BRAGI Update—Arrival of Prototype Chassis Parts—More People—Awesomeness (May 13, 2014).
BRAGI Update—Chinese New Year, Design Verification, Charging Case, More People, Timeline(Mar. 6, 2015).
BRAGI Update—First Sleeves From Prototype Tool—Software Development Kit (Jun. 5, 2014).
BRAGI Update—Let's Get Ready to Rumble, A Lot to Be Done Over Christmas (Dec. 22, 2014).
BRAGI Update—Memories From April—Update on Progress (Sep. 16, 2014).
BRAGI Update—Memories from May—Update on Progress—Sweet (Oct. 13, 2014).
BRAGI Update—Memories From One Month Before Kickstarter—Update on Progress (Jul. 10, 2014).
BRAGI Update—Memories From the First Month of Kickstarter—Update on Progress (Aug. 1, 2014).
BRAGI Update—Memories From the Second Month of Kickstarter—Update on Progress (Aug. 22, 2014).
BRAGI Update—New People @BRAGI-Prototypes (Jun. 26, 2014).
BRAGI Update—Office Tour, Tour to China, Tour to CES (Dec. 11, 2014).
BRAGI Update—Status on Wireless, Bits and Pieces, Testing-Oh Yeah, Timeline(Apr. 24, 2015).
BRAGI Update—The App Preview, The Charger, The SDK, BRAGI Funding and Chinese New Year (Feb. 11, 2015).
BRAGI Update—What We Did Over Christmas, Las Vegas & CES (Jan. 19, 2014).
BRAGI Update—Years of Development, Moments of Utter Joy and Finishing What We Started(Jun. 5, 2015).
BRAGI Update—Alpha 5 and Back to China, Backer Day, On Track(May 16, 2015).
BRAGI Update—Beta2 Production and Factory Line(Aug. 20, 2015).
BRAGI Update—Certifications, Production, Ramping Up.
BRAGI Update—Developer Units Shipping and Status(Oct. 5, 2015).
BRAGI Update—Developer Units Started Shipping and Status (Oct. 19, 2015).
BRAGI Update—Developer Units, Investment, Story and Status(Nov. 2, 2015).
BRAGI Update—Getting Close(Aug. 6, 2014).
BRAGI Update—On Track, Design Verification, How It Works and What's Next(Jul. 15, 2015).
BRAGI Update—On Track, On Track and Gems Overview.
BRAGI Update—Status on Wireless, Supply, Timeline and Open House@BRAGI(Apr. 1, 2015).
BRAGI Update—Unpacking Video, Reviews on Audio Perform and Boy Are We Getting Close(Sep. 10, 2015).
International Search Report & Written Opinion, PCT/EP2016/075113 (dated Feb. 3, 2017).
Last Push Before the Kickstarter Campaign Ends on Monday 4pm CET (Mar. 28, 2014).
Staab, Wayne J., et al., "A One-Size Disposable Hearing Aid is Introduced", The Hearing Journal 53(4):36-41) Apr. 2000.
Stretchgoal—It's Your Dash (Feb. 14, 2014).
Stretchgoal—The Carrying Case for the Dash (Feb. 12, 2014).
Stretchgoal—Windows Phone Support (Feb. 17, 2014).
The Dash + The Charging Case & The BRAGI News (Feb. 21, 2014).
The Dash—A Word From Our Software, Mechanical and Acoustics Team + An Update (Mar. 11, 2014).
Update From BRAGI—$3,000,000—Yipee (Mar. 22, 2014).
Weisiger, "Conjugated Hyperbilirubinemia", (Jan. 5, 2016).
International Preliminary Report on Patentability, PCT/EP2016/075113, dated May 3, 2018, 9 Pages.

* cited by examiner

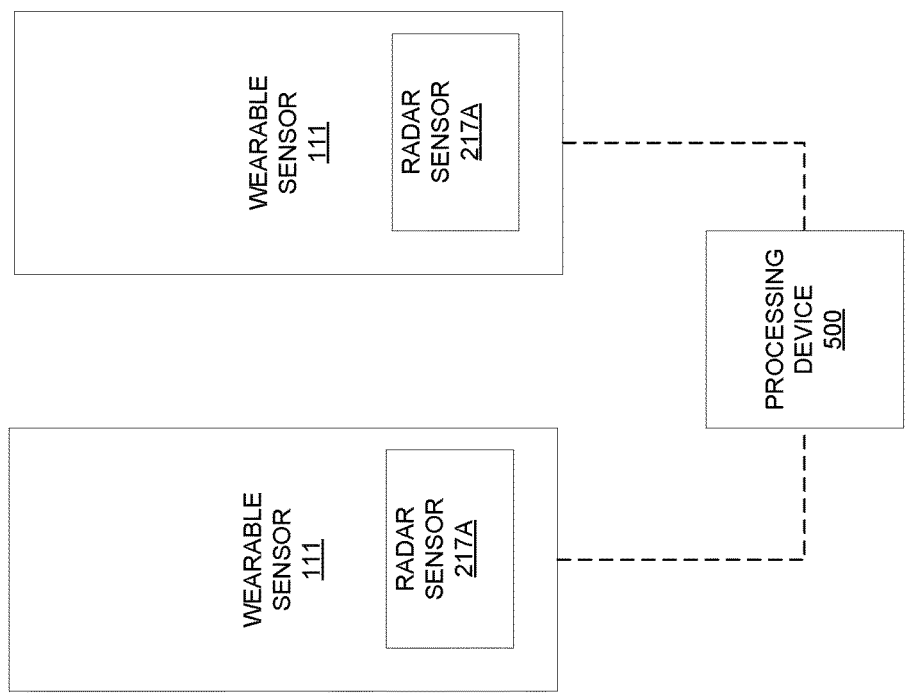

MONITORING PULSE TRANSMISSIONS USING RADAR

PRIORITY STATEMENT

This application is a continuation-in-part and claims priority to U.S. patent application Ser. No. 15/290,459, filed Oct. 11, 2016, hereby incorporated by reference in its entirety. U.S. patent applications Ser. No. 15/290,459 claims priority to U.S. Provisional Patent Application 62/244,147, filed on Oct. 20, 2015, and entitled Personal Area Network Devices System and Method, hereby incorporated by reference in its entirety.

BACKGROUND

I. Field of the Disclosure

The illustrative embodiments relate to personal area networks. More specifically, but not exclusively, the illustrative embodiments relate to wireless earpieces or other wearable devices acting together in order to improve physiological sensing.

II. Description of the Art

The growth of wearable devices is increasing exponentially. This growth is fostered by the decreasing size of microprocessors, circuity boards, chips, and other components. In some cases, wearable devices may obtain biometric sensing data. However, issues remain in reliably sensing biometric parameters. Therefore, problems remain.

SUMMARY OF THE DISCLOSURE

According to one aspect, a method for improving biometric data by using a plurality of wearable devices on a network is provided. The method may include making a first measurement at a first wearable sensor at a first location on a body, making a second measurement at a second wearable sensor positioned at a second location on the body and detecting an arterial pulse wave transit time using the first measurement and the second measurement. The first wearable sensor may be a first radar sensor and the second wearable sensor may be a second radar sensor.

According to another aspect, a method for improving biometric data by using a plurality of wearable devices on a network is provided. The method includes making a first biometric measurement of a first waveform at a first wearable sensor at a first location on a body, making a second biometric measurement of a second waveform at a second wearable sensor positioned at a second location on the body, and analyzing the first biometric measurement of the first waveform and the second biometric measurement of the second waveform at a processing device in order to provide biometric data.

BRIEF DESCRIPTION OF THE DRAWINGS

Illustrated embodiments of the present invention are described in detail below with reference to the attached drawing figures, which are incorporated by reference herein, and where:

FIG. 5 illustrates two wearable sensors with radar sensors in operative communication with one another.

DETAILED DESCRIPTION OF THE DISCLOSURE

The illustrative embodiments provide a system, method, and personal area network which may include two or more wearable sensors which may sense and communicate information between each other or to other devices. This information may include biometric data. In some instances, biometric data from different wearable sensors is combined together. For example, pulse waveforms from different sensors may be combined to provide pulse wave transit times. In one embodiment, the personal area network may include wireless earpieces. The wireless earpieces may be utilized to control, communicate, manage, or interact with a number of other wearable devices, such as smart glasses, watches, jewelry, implants, displays, clothing, or so forth which may include one or more sensors such as biometric sensors. A personal area network is a network for data transmissions among devices, such as personal computing, communications, camera, vehicles, entertainment, and medical devices. The personal area network may utilize any number of wired, wireless, or hybrid configurations and may be stationary or dynamic. For example, the personal area network may utilize wireless network protocols or standards, such as INSTEON, IrDA, Wireless USB, Bluetooth, Z-Wave, ZigBee, Wi-Fi, or other developing standards. In some embodiments device may communicate with each other through magnetic induction.

The wireless earpieces may include any number of sensors for receiving user input and converting the user input into commands or selections made across the personal devices of the personal area network. For example, the user input of the wireless earpieces may include voice commands, head motions, finger taps, finger swipes or motions, position, location, or other user inputs sensed by the wireless earpieces. The user input may be determined and converted into commands that may be sent to one or more external devices, such as the smart glasses. In one embodiment, the user input may be utilized to send a command that controls content that is displayed by smart glasses communicatively linked with the wireless earpieces. For example, the user may select to display content, scroll, zoom, dismiss, or implement other actions selected by the user. The user may be able to augment their worldview and expand the field of vision utilizing the personal area network devices.

Figure 1:
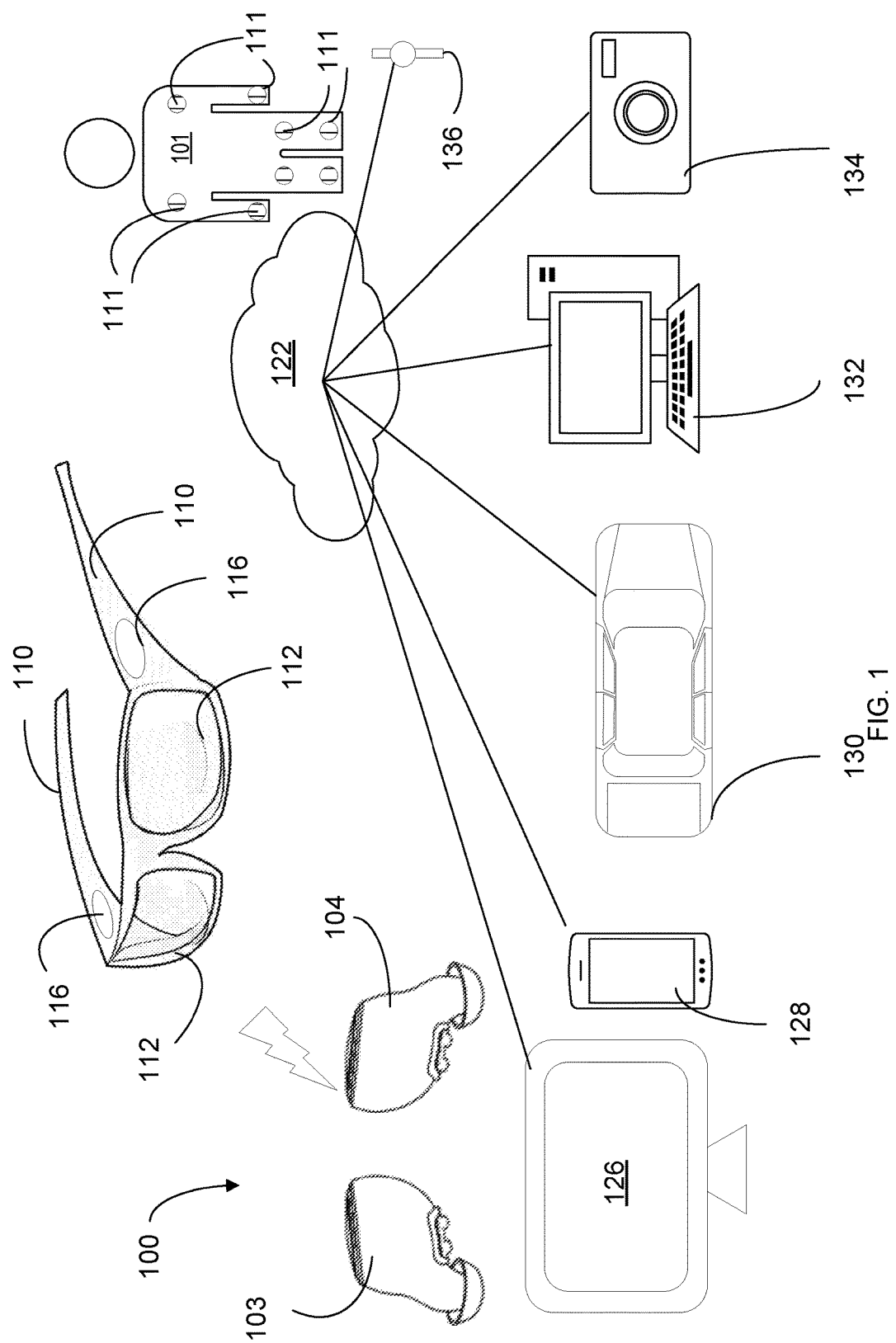
FIG. 1 is a pictorial representation of a communication system in accordance with an illustrative embodiment.

FIG. 1 is a pictorial representation of a communication system 100 in accordance with an illustrative embodiment. In one embodiment, the communication system 100 may represent a personal area network utilized by a user. The communication system 100 may also represent any number of systems, environments, or networks in which a user may utilize the described devices and components.

In one embodiment, the communication system 100 utilized by a user 101 may include wireless earpieces 102, including a left earpiece 103, and a right earpiece 104, a wireless signal 106, smart glasses 110, network 122, wireless signals 124, a display 126, a wireless device 128, a vehicle 130, a computer 132, a camera 134, and a smart watch 136. The wireless earpieces 102 are configured to fit into ears of a user 101. The wireless earpieces 102 are shown separately from their positioning within the ears of the user 101 for purposes of simplicity.

In one embodiment, the wireless earpieces 102 include a frame shaped to fit substantially within the ear of the user. The frame is a support structure that at least partially encloses and houses the electronic components of the wireless earpieces 102. The frame may include one or more sleeves configured to fit the inside of the ear of the user 101. The wireless earpieces 102 may be configured to play music or audio, receive and make phone calls or other communications, determine ambient environmental conditions (e.g., temperature, altitude, location, speed, heading, etc.), read user biometrics (e.g., heart rate, motion, sleep, blood oxygenation, calories burned, etc.), and receive user input, feedback, or instructions.

The devices of the communication system 100 may include any number of devices, components, or so forth that may communicate with each other through a wireless (or wired) connection, signals, or link, such as the wireless signals 106 and 124. The network 122 may include any number of network components and devices, such as routers, servers, signal extenders, intelligent network devices, computing devices, or so forth. In one embodiment, the network 122 represents a personal area network as previously disclosed. Communications, such as the wireless signals 106 and 124, within the communication system 100 may occur through the network 122 or may occur directly between devices, such as the wireless earpieces 102 and the smart glasses 110 (e.g., direct communication of the wireless signal 106) or between the wireless earpieces 102 and the wireless device 128 (indirect communication through the network 122 utilizing the wireless signal 124). In one embodiment, the network 122 may communicate with or include a wireless network, such as a Wi-Fi, cellular (e.g., 3G, 4G, 5G, PCS, GSM, etc.), Bluetooth, or other radio frequency network. The network 122 may also communicate with any number of hard wired networks, such as local area networks, coaxial networks, fiber-optic networks, or so forth. Communications within the communication system 100 may be operated by one or more users, service providers, or network providers.

The smart glasses 110 are a wearable computer that adds information to what the wearer naturally sees. In one embodiment, the smart glasses 110 may include an optical head-mounted display (OHMD), a computerized Internet connected glasses with transparent heads up display (HUD), or an augmented reality overlay that has the capability of reflecting projected digital images. In another embodiment, the smart glasses 110 may represent virtual reality or holographic display devices (e.g., devices produced by Oculus VR, Sony, Microsoft, Google, etc.). The smart glasses may include a frame 114 and logical components 116. The frame 114 may be the support structure of the smart glasses 110. In one embodiment, the frame 114 may be physically connected across the lenses 112 and bridge. In one embodiment, the logical components 116 are embedded or integrated with the frame 114. For example, the logical components 116 may be removed for upgrading the smart glasses 110 over time. The logical components 116 may include any number of components including one or more batteries, memories, logic units (e.g., processors, ASICs, FPGAs, digital logic, etc.), transceivers, cameras, speakers, motherboards, circuits, contacts, ports, adapters, connectors, or so forth. The logical components 116 may be connected to the different components within the smart glasses 110 utilizing any number of traces, contacts, wires, busses, or so forth. The connection components may be transparent or positioned to minimize visibility (e.g., within the lenses 112).

In one embodiment, the lenses 112 may be a transparent display that presents data without requiring the user 101 to look away from his/her usual viewpoints. The lenses 112 may be transparent displays for displaying information and content to the user 101. For example, the lenses 112 may include electronic glass for displaying content for the user 101. For example, the lenses 112 may display content that is displayed in a single direction toward the user 101 such that the displayed content is not visible on the other side of the smart glasses 110 to preserve confidentiality of the content and privacy of the user 101. In one embodiment, interactive content may be displayed across an entire surface of the lenses 112. In another embodiment, the content may be display on one or more designated segments, such as segments 118. The smart glasses 110 are configured to allow the user full access to real world content while still displaying other content which may include graphics, data, programs, augmented reality content, or other information. The lenses 112 may provide full view to the user's surroundings as well as to focused views of various data streams communicated to the smart glasses 110 and available through the personal area network of the user 101.

The lenses 112 may also be adaptive optics that change the focal length or provide augmented views of the surroundings. In one embodiment, the lenses 112 may include liquid display components (adjustable focus eyeglasses) that may dynamically reconfigure the shape of the lenses 112 specifically for the user 101. For example, focal points and characteristics of the eye of the user 101 may be utilized to adjust the lenses 112 by adjust a current or voltage applied across the lenses 112. For example, the lenses 112 may be reshaped or provide additional contrast, color enhancement, or so forth for the user 101. This may be particularly useful for users with disabilities or users in difficult situations, such as firemen, police officers, military personnel, security, or so forth. The lenses 112 may be utilized to help correct myopia, hyperopia, presbyopia, and other eye conditions and diseases.

Content displayed by the smart glasses 110 may be controlled by the user 101 utilizing voice commands received through microphones of the wireless earpieces 102, smart glasses, or other devices of the network 122 (e.g., smart television 126, wireless device 128, vehicle 130, etc.). In one embodiment, different or distinct content may be displayed by each of the lenses 112 (i.e., left lens and right lens). For example, audible commands may be directed to the wireless earpieces 102 that may be converted to instructions for displaying content on the lenses 112, such as "display a map on the left and a trip timer on the right".

As noted, both the smart glasses 110 and the wireless earpieces 102 may include a number of sensors including touch sensors, optical sensors, pulse oximeters, microphones, accelerometers, gyroscopes, global positioning chips, radar sensors, lidar sensors, and so forth for detecting the biometrics, motion, location, and activities of the user. The information may be utilized to coordinate the audio, video, text, and graphical information presented to the user 101 by the wireless earpieces 102 and the smart glasses 110. For example, the user 101 may select to dismiss content by tilting her head to the left. In one embodiment, the user 101 may program the smart glasses 110 and/or the wireless earpieces 102 to perform specific activities in response to a user motion, command or audio signal, or other action. As a result, the communication system 100 may be adapted to the needs and desires of the user 101.

In another embodiment, logical components 116 may utilize one or more projectors 115, such as a scanning laser or other components to display or reflect images directly or indirectly on the lenses 112. For example, one or more projectors 115 may project content onto the lenses 112. In one embodiment, the projectors 115 may be integrated into a portion of the frame 114, the lenses 112, or the logical components 116. The focus, direction, size, and so forth may be adapted so that the content may be properly viewed by the user (whether displayed on the lenses 112 or refracted to the eyes of the user 101).

In another embodiment, the projectors 115 may include cameras for tracking the eye movements of the user 101. The eye movements may be utilized to make selections, receive user input, or otherwise select content for display by the smart glasses 110. For example, the user 101 may switch between applications, information, or data sets by looking (e.g., tracking retina motion) at specific content, performing specified eye movements, blinking commands, or so forth. In another embodiment, the cameras may also be utilized to use other user 101 clues or actions, such as facial expressions (e.g., motion or shape of the eyes, mouth, eyebrows, cheeks, etc.), hand motions, or other activities to implement specific commands. In another embodiment, the cameras may face forward and may utilize various wavelengths and spectra to enhance the vision of the user 101. For example, infrared, thermal, or other optical or image sensors may take in images and then project those images onto the lenses 112 for viewing by the user 101.

In one embodiment, the smart glasses 110 may utilize short-range or long-range wireless communications to communicate with the wireless earpieces 102 through the wireless signal 106 or devices of the network 122 through the wireless signal 124. For example, the smart glasses 110 may include a Bluetooth and cellular transceiver within the logical components 116. In one embodiment, the smart glasses 110 may communicate with the wireless earpieces 102 through the wireless signal 106. For example, the wireless signal 106 may be a Bluetooth, Wi-Fi, Zigbee, Ant+, or other short range wireless communication. The smart glasses 110 may include any number of logical components 112. In another embodiment, the smart glasses 110 may be configured to physically connect to or integrate with the wireless earpieces 102. For example, small flexible connectors may be connected to ports of the wireless earpieces 102. Flexible connectors, such as wires may act as lanyards for the wireless earpieces 102. In another embodiment, the wireless earpieces 102 may connect to the frame 114 to fit in the ears of the user 101. For example, magnetic connectors may electrically and physically interface the wireless earpieces with the smart glasses 110 for enhanced functionality (e.g., communications, battery life, synchronization, etc.).

The display 126 may represent any number of displays, such as monitors, televisions, smart televisions, projectors, holographic displays, or so forth. The wireless earpieces 102 may control content displayed to any of the devices of the communication system 100. The display 126 may also represent any number of wearable displays or mobile displays that may be utilized by the user 101.

The wireless device 128 may represent any number of wireless electronic devices, such as smart phones, laptops, gaming devices, music players, personal digital assistants, vehicle systems, or so forth. The wireless device 128 may communicate utilizing any number of wireless connections, standards, or protocols (e.g., near field communications, Bluetooth, Wi-Fi, ANT+, etc.). For example, the wireless device 128 may be a touch screen cellular phone that communicates with the wireless earpieces 102 utilizing Bluetooth communications. The wireless device 128 may implement and utilize any number of operating systems, kernels, instructions, or applications that may make use of the sensor data or user input received from the wireless earpieces 102. For example, the wireless device 128 may represent any number of android, iOS, Windows, open platforms, or other systems. Similarly, the wireless device 128 may include a number of applications that utilize the user input, biometric data, and other feedback from the wireless earpieces 102 to display applicable information and data, control the applications, or make other selections. For example, biometric information (including, high, low, average, or other values) may be processed by the wireless earpieces 102 or the wireless device 128 to display heart rate, blood oxygenation, altitude, speed, distance traveled, calories burned, or other applicable information.

In one embodiment, the wireless device 128 may include any number of input components and sensors (e.g., similar to those described with regard to the wireless earpieces 102) that may be utilized to augment the input and sensor readings of the wireless earpieces 102. For example, a microphone of the wireless device 128 may determine an amount and type of ambient noise. The noise may be analyzed and utilized to filter the sensor readings made by the wireless earpieces 102 to maximize the accuracy and relevance of the sensor measurements of the wireless earpieces 102. For example, the wireless earpieces 102 may adjust the information that is displayed visually to the smart glasses 110 in response to extremely noisy environments (e.g., showing a visual indicator to turn in loud environments, a blind spot indicator, etc.). Filtering, tuning, and adaptation for the sensor measurements may be made for signal noise, electronic noise, or acoustic noise, all of which are applicable in the communication system 100. Sensor measurements made by either the wireless earpieces 102, wireless device 128, or sensor devices of the user 101 may be communicated with one another in the communication system 100. The wireless device 128 is representative of any number of personal computing, communications, exercise, medical, or entertainment devices that may communicate with the wireless earpieces 102.

The vehicle 130 may include any number of computing, communications, entertainment, and control systems that may be integrated with or utilized within the vehicle 130. For example, the wireless earpieces 102 may receive music streamed from the vehicle 130. The wireless earpieces 102 may also control vehicle systems, such as GPS, car locks (e.g., doors, truck, windows, panels, trunk, etc.), window controls, emergency systems, music and video systems, telephone features, performance tuning, and so forth.

The camera 134 and computer 132 may also receiving information, data, and commands form the wireless earpieces 102. In one embodiment, the user 101 may send an audio command to the camera 134 to take a picture of the user 101 and her family posed in front of the camera 134. In another embodiment, the user 101 may dictate content or control programs and operation of the computer 132 through the wireless earpieces 102.

The camera 134 may also represent one or more cameras or a camera system. For example, the camera 134 may represent an array of personal cameras that provide multiple views around the periphery (e.g., side views, behind, etc.) of the user 101. The user 101 may move her eyes or head to change views displayed by the smart glasses 110 between the different views of the camera. Displaying different views provided by the camera 134 may be useful for bikers, vehicles, police officers, or so forth. In one embodiment, the logic 116 may include cameras that look out to the sides of the user 101 when worn. Additionally, the frame 114 may include cameras at the end of the earpieces that look backward to provide a rear/side view for the user. Additional cameras may be utilized to provide a three hundred and sixty degree view around the user 101 at all times utilizing the wireless earpieces. The different views may be communicated to portions of the lenses 112.

With respect to the wireless earpieces 102, sensor measurements or user input may refer to measurements made by one or both of the wireless earpieces 102. For example, the wireless earpieces 102 may determine that user input of a sensor in the right wireless earpiece 104 is very noisy and, as a result, may utilize the sensor signal from the sensors of the left wireless earpiece 103 as the primary measurement. The wireless earpieces 102 may also switch back and forth between sensors of the left and right wireless earpieces 104, 103 in response to varying noise for both of the wireless earpieces 102. As a result, the clearest sensor signal may be utilized at any given time. In one embodiment, the wireless earpieces 102 may switch sensor measurements in response to the sensor measurements exceeding or dropping below a specified threshold.

The user 101 may also be wearing or carrying any number of sensor-enabled devices, such as heart rate monitors, pacemakers, smart glasses, smart watches or bracelets (e.g., Apple watch, Fitbit, etc.), or other sensory devices that may be worn, attached to, or integrated with the user 101. The data and information from the external sensor devices may be communicated to the wireless earpieces 102. In another embodiment, the data and information from the external sensor devices may be utilized to perform additional processing of the information sent from the wireless earpieces 102 to the wireless device 128. Other examples of body mounted sensors including a display are shown in Boesen U.S. Pat. Nos. 6,470,893 and 6,823,195 which are hereby incorporated by reference and may also be integrated or utilized within the communication system 100.

The sensors of the wireless earpieces 102 may also be positioned at enantiomeric locations. For example, a number of colored light emitting diodes may be positioned to provide variable data and information, such as heart rate, respiratory rate, and so forth. The data gathered by the LED arrays may be sampled and used alone or in aggregate with other sensors. As a result, sensor readings may be enhanced and strengthened with additional data.

The user 101 may also wear a smart watch 136 (e.g., Apple, Samsung, Sony smart watches, etc.). The smart watch 136 (or other wearable sensor) may utilize biopotential sensing to determine various user 101 biometrics. The user 101 may view the data on the smart glasses 110 when viewing the smart watch 136 is inconvenient or not possible. The data from the smart watch 136 may be displayed remotely on the lenses 112 of the smart glasses 110 and/or played audibly to the user 101 utilizing the speakers of the wireless earpieces 102. Any of the devices of the communication system 100 may also push data to the other devices in contact with the user 101 directly or through the network 122, such as from the smart watch 136 to an in-vehicle display of the vehicle 130 (which may represent a car, motorcycle, bicycle, boat, plane, bus, etc.).

In another embodiment, the wireless earpieces 102 may represent wireless devices that may be ingested or implanted into a user. For example, the described electronics may be endoscopic pills, pacemakers, tracking devices, contact lenses, oral implants, bone implants, artificial organs, or so forth.

In addition, a user may wear one or more wearable sensors 111 in addition to the earpieces 100 and glasses, and/or watch 136. The wearable sensors 111 may include one or more radar sensors. The radar sensors may use single chip integrated radar sensors or may be otherwise constructed. The wearable sensors 111 with radar sensors may be used to detect small movements or micro-movements associated with the human anatomy, amongst other applications. It is to be understood that it is advantageous to have multiple wearable sensors 111 present and that the wearable sensors may communicate data between each other or over a body area network or to another device with processing capabilities such as the earpieces 100.

One application where the wearable sensors may be used is in determining pulse transmit times. According to one definition, a pulse transmit time is the time it takes the Pulse Pressure (PP) waveform to propagate through a length of the arterial tree. The pulse pressure waveform results from the ejection of blood from the left ventricle and moves with a velocity much greater than the forward movement of the blood itself. Two or more sensors positioned at different locations within the body may be used to measure pulse and where the two or more sensors are along a length of the arterial tree, measurements from the different sensors may be used together in order to calculate pule transmit times. Additional biometric information may also be determined using the pulse transmit time such as pulse wave velocity.

As shown in FIG. 1, wearable sensors 111 may be positioned along different portions of the body at different locations. In addition, to the wearable sensors 111 shown, it is to be understood that sensors which may be used within the earpieces, glasses, watches, or other wearable devices. Where radar sensors are used, the radar sensors may be used to monitor real-time biometric data such as heart rate, breathing rate, and movement.

Figure 2:
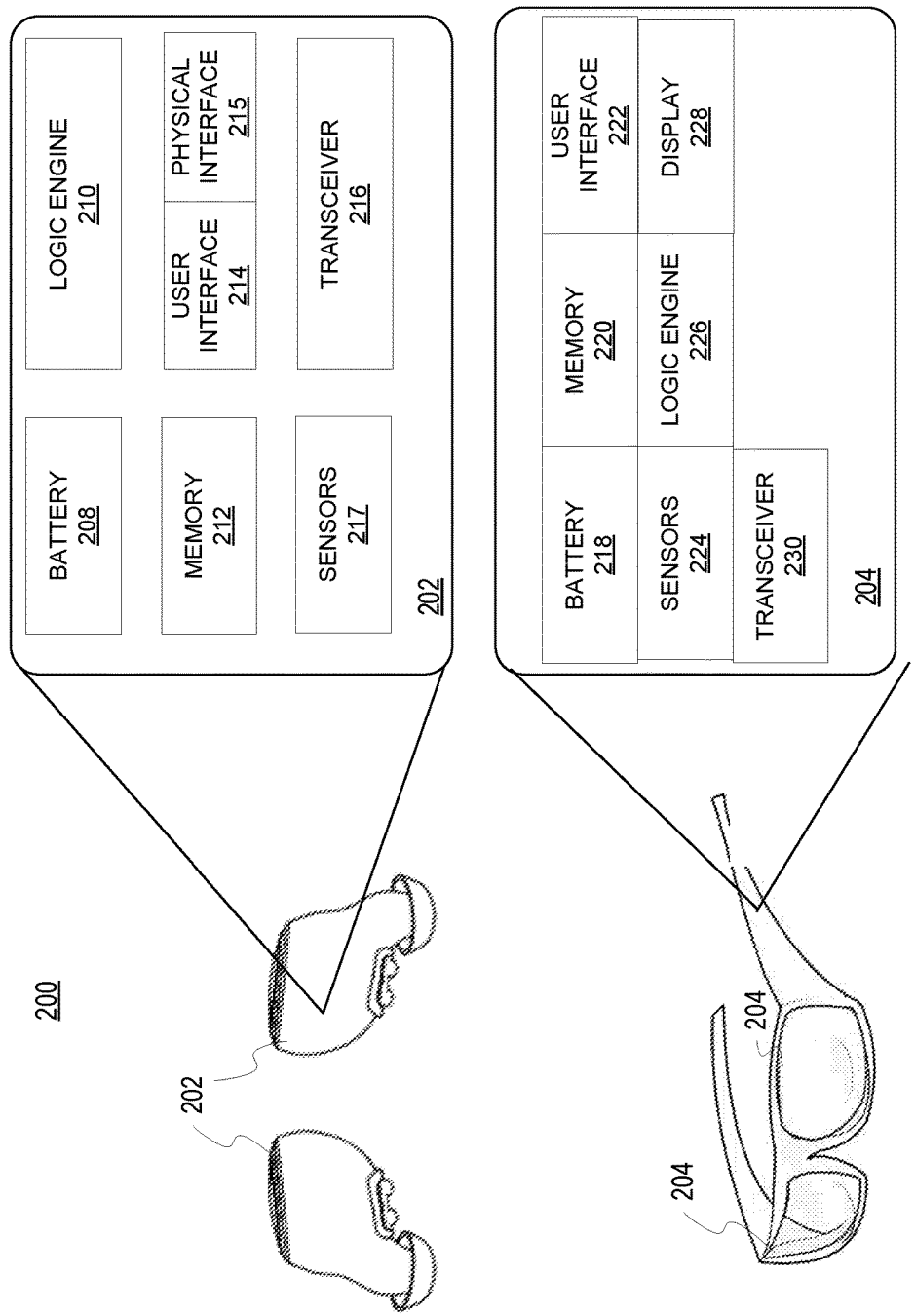
FIG. 2 is a block diagram of wireless earpieces and smart glasses in accordance with an illustrative embodiment.

FIG. 2 is a block diagram of a wireless earpiece system 200 in accordance with an illustrative embodiment. In one embodiment, the wireless earpiece system 200 may include wireless earpieces 202 (described collectively rather than individually) and smart glasses 204. In one embodiment, the wireless earpiece system 200 may enhance communications and functionality of the wireless earpieces 202.

As shown, the wireless earpieces 202 may be wirelessly linked to the smart glasses 204. User input and commands may be received from either the wireless earpieces 202 or the smart glasses 204 for implementation on either of the devices of the wireless earpiece system 200 (or other externally connected devices). As previously noted, the wireless earpieces 102 may be referred to or described herein as a pair (wireless earpieces) or singularly (wireless earpiece). The description may also refer to components and functionality of each of the wireless earpieces 202 collectively or individually.

In some embodiments, the smart glasses 204 may act as a logging tool for receiving information, data, or measurements made by the wireless earpieces 202. For example, the smart glasses 204 may be worn by the user to download data from the wireless earpieces in real-time. As a result, the smart glasses 204 may be utilized to store, display, and synchronize data for the wireless earpieces 202. For example, the smart glasses 204 may display pulse, oxygenation, distance, calories burned, and so forth as measured by the wireless earpieces 202. The wireless earpieces 202 and the smart glasses 204 may have any number of electrical configurations, shapes, and colors and may include various circuitry, connections, and other components.

In one embodiment, the wireless earpieces 202 may include a battery 208, a logic engine 210, a memory 212, user interface 214, physical interface 215, a transceiver 216, and sensors 212. The smart glasses 204 may have a battery 218, a memory 220, an interface 222, and sensor or sensors 224. The battery 208 is a power storage device configured to power the wireless earpieces 202. Likewise, the battery 218 is a power storage device configured to power the smart glasses 204. In other embodiments, the batteries 208 and 218 may represent a fuel cell, thermal electric generator, piezo electric charger, solar charger, ultra-capacitor, or other existing or developing power storage technologies.

The logic engine 210 is the logic that controls the operation and functionality of the wireless earpieces 202. The logic engine 210 may include circuitry, chips, and other digital logic. The logic engine 210 may also include programs, scripts, and instructions that may be implemented to operate the logic engine 210. The logic engine 210 may represent hardware, software, firmware, or any combination thereof. In one embodiment, the logic engine 210 may include one or more processors. The logic engine 210 may also represent an application specific integrated circuit (ASIC) or field programmable gate array (FPGA). The logic engine 210 may be utilize information and from the sensors 212 to determine the biometric information, data, and readings of the user. The logic engine 202 may utilize this information and other criteria to inform the user of the biometrics (e.g., audibly, through an application of a connected device, tactilely, etc.).

The logic engine 210 may also process user input to determine commands implemented by the wireless earpieces 202 or sent to the wireless earpieces 204 through the transceiver 216. The user input may be determined by the sensors 217 to determine specific actions to be taken. In one embodiment, the logic engine 210 may implement a macro allowing the user to associate user input as sensed by the sensors 217 with commands.

In one embodiment, a processor included in the logic engine 210 is circuitry or logic enabled to control execution of a set of instructions. The processor may be one or more microprocessors, digital signal processors, application-specific integrated circuits (ASIC), central processing units, or other devices suitable for controlling an electronic device including one or more hardware and software elements, executing software, instructions, programs, and applications, converting and processing signals and information, and performing other related tasks. The processor may be a single chip or integrated with other computing or communications elements of the smart case 202.

The memory 212 is a hardware element, device, or recording media configured to store data for subsequent retrieval or access at a later time. The memory 212 may be static or dynamic memory. The memory 212 may include random access memory, cache, removable media drive, mass storage, or configuration suitable as storage for data, instructions, and information. In one embodiment, the memory 212 and the logic engine 210 may be integrated. The memory may use any type of volatile or non-volatile storage techniques and mediums. The memory 212 may store information related to the status of a user, wireless earpieces 202, smart glasses 204, and other peripherals, such as a wireless device, smart case for the wireless earpieces 202, smart watch, and so forth. In one embodiment, the memory 212 may display instructions or programs for controlling the user interface 714 including one or more LEDs or other light emitting components, speakers, tactile generators (e.g., vibrator), and so forth. The memory 212 may also store the user input information associated with each command.

The transceiver 216 is a component comprising both a transmitter and receiver which may be combined and share common circuitry on a single housing. The transceiver 216 may communicate utilizing Bluetooth, Wi-Fi, ZigBee, Ant+, near field communications, wireless USB, infrared, mobile body area networks, ultra-wideband communications, cellular (e.g., 3G, 4G, 5G, PCS, GSM, etc.) or other suitable radio frequency standards, networks, protocols, or communications. The transceiver 216 may also be a hybrid transceiver that supports a number of different communications. For example, the transceiver 216 may communicate with the smart glasses 204 or other systems utilizing wired interfaces (e.g., wires, traces, etc.), NFC or Bluetooth communications.

The components of the wireless earpieces 202 (or the wireless earpiece system 200) may be electrically connected utilizing any number of wires, contact points, leads, busses, wireless interfaces, or so forth. In addition, the wireless earpieces 202 may include any number of computing and communications components, devices or elements which may include busses, motherboards, circuits, chips, sensors, ports, interfaces, cards, converters, adapters, connections, transceivers, displays, antennas, and other similar components. The physical interface 215 is hardware interface of the wireless earpieces 202 for connecting and communicating with the smart glasses 204 or other electrical components.

The physical interface 215 may include any number of pins, arms, or connectors for electrically interfacing with the contacts or other interface components of external devices or other charging or synchronization devices. For example, the physical interface 215 may be a micro USB port. In one embodiment, the physical interface 215 is a magnetic interface that automatically couples to contacts or an interface of the smart glasses 204. In another embodiment, the physical interface 215 may include a wireless inductor for charging the wireless earpieces 202 without a physical connection to a charging device.

The user interface 214 is a hardware interface for receiving commands, instructions, or input through the touch (haptics) of the user, voice commands, or predefined motions. The user interface 214 may be utilized to control the other functions of the wireless earpieces 202. The user interface 214 may include the LED array, one or more touch sensitive buttons or portions, a miniature screen or display, or other input/output components. The user interface 214 may be controlled by the user or based on commands received from the smart glasses 204 or a linked wireless device.

In one embodiment, the user may provide feedback by tapping the user interface 214 once, twice, three times, or any number of times. Similarly, a swiping motion may be utilized across the user interface 214 (e.g., the exterior surface of the wireless earpieces 202) to implement a predefined action. Swiping motions in any number of directions may be associated with specific activities, such as play music, pause, fast forward, rewind, activate a digital assistant (e.g., Siri, Cortana, smart assistant, etc.). The swiping motions may also be utilized to control actions and functionality of the smart glasses 204 or other external devices (e.g., smart television, camera array, smart watch, etc.). The user may also provide user input by moving her head in a particular direction or motion or based on the user's position or location. For example, the user may utilize voice commands, head gestures, or touch commands to change the content displayed by the smart glasses 204.

The sensors 217 may include pulse oximeters, accelerometers, gyroscopes, magnetometers, inertial sensors, photo detectors, miniature cameras, and other similar instruments for detecting location, orientation, motion, and so forth. The sensors 217 may also be utilized to gather optical images, data, and measurements and determine an acoustic noise level, electronic noise in the environment, ambient conditions, and so forth. The sensors 217 may provide measurements or data that may be utilized to filter or select images for display by the smart glasses 204. For example, motion or sound detected on the left side of the user may be utilized to command the smart glasses to display camera images from the left side of the user. Motion or sound may be utilized, however, any number of triggers may be utilized to send commands to the smart glasses 204.

The smart glasses 204 may include components similar in structure and functionality to those shown for the wireless earpieces 202 including a battery 218, a memory 220, a user interface 222, sensors 224, a logic engine 226, a display 228, and transceiver 230. The smart glasses 204 may include the logic engine 226 for executing and implementing the processes and functions as are herein described. The battery 218 of the smart glasses 204 may be integrated into the frames of the smart glasses 204 and may have extra capacity which may be utilized to charge the wireless earpieces 202. For example, the wireless earpieces 202 may be magnetically coupled or connected to the smart glasses 204 so that the battery 218 may be charged. All or a portion of the logic engine 226, sensors, user interface 222, sensors 224, display, and transceiver 230 may be integrated in the frame and/or lenses of the smart glasses 204.

The user interface 222 of the smart glasses 204 may include a touch interface or display for indicating the status of the smart glasses 204. For example, an external LED light may indicate the battery status of the smart glasses 204 as well as the connected wireless earpieces 202, connection status (e.g., linked to the wireless earpieces 202, wireless device, etc.), download/synchronization status (e.g., synchronizing, complete, last synchronization, etc.), or other similar information.

The display 228 may be integrated into the lenses of the smart glasses 204 or represent one or more projectors that may project content directly or reflectively to the eyes of the user. For example, the display 228 may represent a transparent organic light emitting diode lens that is see through and may be utilized to display content. Projectors of the display 228 may utilize any number of wavelengths or light sources to display data, images, or other content to the user.

An LED array of the user interface 222 may also be utilized for display actions. For example, an LED may be activated in response to someone or something being in the user's blind spot while riding a bicycle. In another embodiment, device status indications may emanate from the LED array of the wireless earpieces 202 themselves, triggered for display by the user interface 222 of the smart glasses 204. The battery 218 may itself be charged through a physical interface of the user interface 222. The physical interface may be integrated with the user interface 222 or may be a separate interface. For example, the user interface 222 may also include a hardware interface (e.g., port, connector, etc.) for connecting the smart glasses 204 to a power supply or other electronic device. The user interface 222 may be utilized for charging as well as communications with externally connected devices. For example, the user interface 222 may represent a mini-USB, micro-USB or other similar miniature standard connector. In another embodiment, a wireless inductive charging system may be utilized to initially replenish power to the wireless earpieces 202. The smart glasses 204 may also be charged utilizing inductive charging.

In another embodiment, the smart glasses 204 may also include sensors for detecting the location, orientation, and proximity of the wireless earpieces 202. For example, the smart glasses 204 may include optical sensors or cameras for capturing images and other content around the periphery of the user (e.g., front, sides, behind, etc.). The smart glasses 204 may detect any number of wavelengths and spectra to provide distinct images, enhancement, data, and content to the user. The smart glasses 204 may also include an LED array, galvanic linkage or other touch sensors, battery, solar charger, actuators or vibrators, one or more touch screens or displays, an NFC chip, or other components.

As originally packaged, the wireless earpieces 202 and the smart glasses 204 may include peripheral devices such as charging cords, power adapters, inductive charging adapters, solar cells, batteries, lanyards, additional light arrays, speakers, smart case covers, transceivers (e.g., Wi-Fi, cellular, etc.), or so forth.

Figure 3:
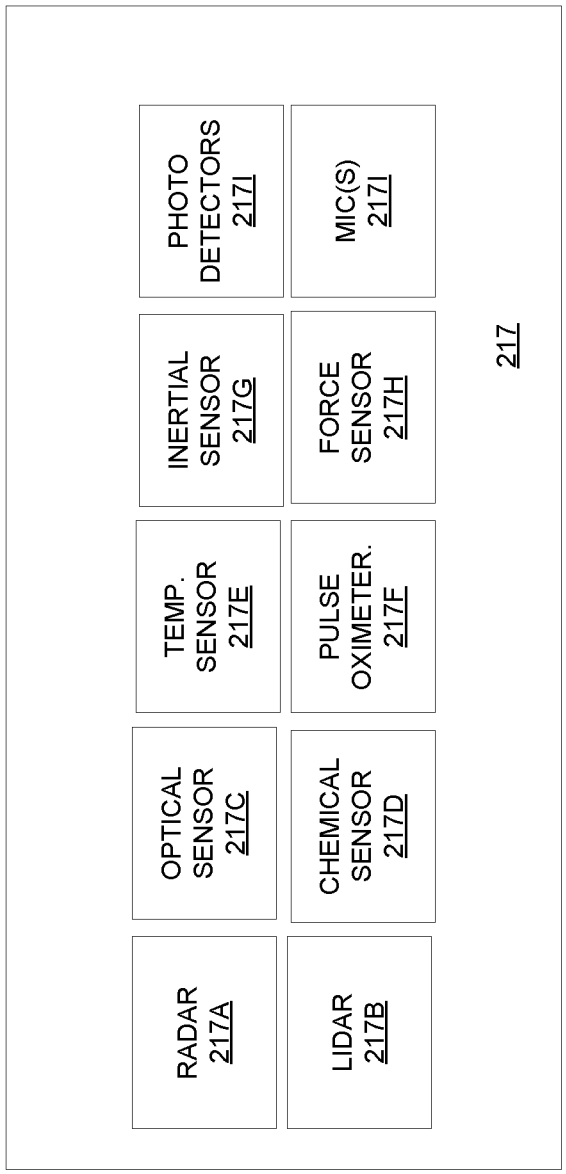
FIG. 3 illustrates various types of sensors within an earpiece.

FIG. 3 illustrates a further example of types of sensors 217 such as may be found in the ear pieces. The sensors 217 may include pulse oximeters, accelerometers, gyroscopes, magnetometers, water, moisture, or humidity detectors, impact/force detectors, chemical sensors (e.g., analysis of sweat, blood, etc.), thermometers, inertial sensors, photo detectors, miniature cameras, microphones, and other similar instruments for detecting the user's status as well as location, utilization of the wireless earpieces 202, orientation, motion, and so forth. The sensors 217 may also be utilized to determine the biometric, activity, location, and speed measurements of the user. In one embodiment, the sensors 217 may store data that may be shared with other components (e.g., logic engine 210), users, and devices.

The sensors 217 may include photodetectors, ultrasonic mapping devices, lidar, or radar that scan the ear of the user when positioned for utilization. The sensors 217 may generate a two or three dimensional scan or topography map of the user's ear and surrounding areas when the wireless earpieces 202 are properly positioned. The mapping may include the internal and/or external portions of the user's ear. The topographical image of the user's ear may be utilized as a stand-alone biometric identifier or may be utilized with other biometric identifiers to identify the user. The image may include the external auditory meatus, scapha, fossa triangularis, scaphoid fossa, helix, antihelix, antitragus, lobule, the tragus, and pinna as well as other internal or external portions of the ear and surrounding head structure.

Where the sensors 217 include radar sensors 217A, the radar sensors 217A may be single chip radar sensors or may be integrated with other integrated circuits on the device. The radar sensor 217A may be used to provide for biometric monitoring through picking up movements including small, subtle, or micro-movements. One example of such a movement is movement of a tympanic membrane. The radar sensor 217A may be oriented towards the inner ear and may be used to detect movement of the tympanic membrane. The radar sensor 217A may be oriented towards the skin of the user and used to determine movements associated with pulse or heart rate. The radar sensor 217A may be otherwise oriented for other purposes such as directed outwardly to detect obstacles or possible collisions in advance.

Where the sensors 217 include lidar sensors 217B, the lidar sensors 217B may be single chip lidar sensors or may be integrated with other integrated circuits on the device. The lidar sensor 217B may be used to provide for biometric monitoring. For example, the lidar sensor 217B may be positioned to scan an inner portion of an ear of the user. Thus, the inner ear portion of a user may be mapped. This may be used in order to identify a user or to observe changes in ear structure over time including differences in cerumen amount or location. It may also aid a user by determining whether the earpiece is positioned correctly within the ear.

Other types of sensors include optical sensors 217C, chemical sensors 217D, temperature sensors 217E, pulse oximeters 217F, inertial sensors 217G which may include accelerometers, magnetometers, compasses, or other inertial sensors, force sensors 217H, photo detectors 217I, and microphones 217J which may include air conduction microphones and/or bone conduction microphones.

Figure 4:
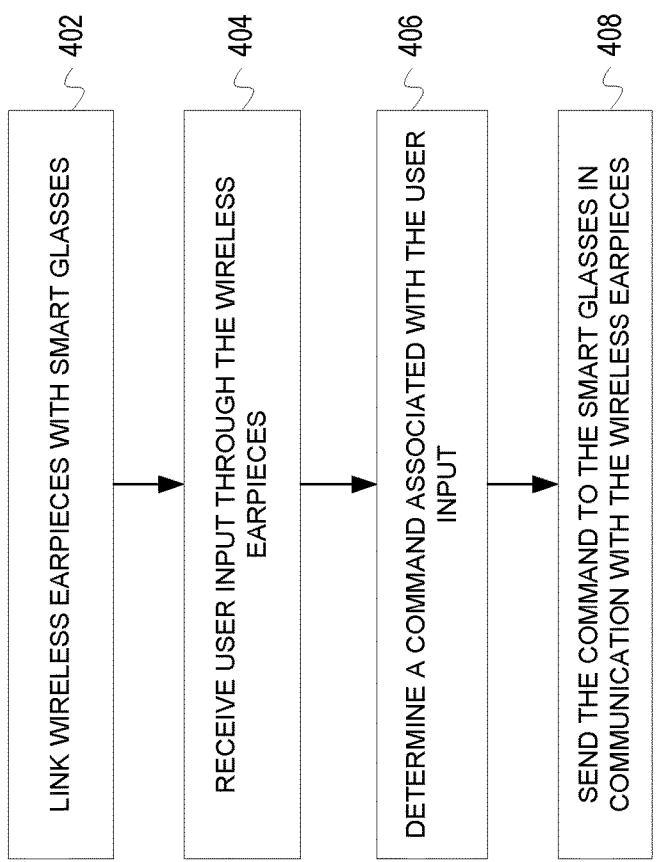
FIG. 4 is a flowchart of a process for controlling smart glasses utilizing wireless earpieces in accordance with an illustrative embodiment.

FIG. 4 is a flowchart of a process for controlling smart glasses utilizing wireless earpieces in accordance with an illustrative embodiment. The process of FIG. 4 may be implemented by one or more wireless earpieces, smart glasses, and any number of other devices communicating directly or through a personal area network.

In one embodiment, the process of FIG. 4 may begin by linking wireless earpieces with smart glasses (step 302). The wireless earpieces may be linked with the smart glasses utilizing any number of communications, standards, or protocols. For example, the devices may be linked by a Bluetooth connection. The process may require that the devices be paired utilizing an identifier, such as a passcode, password, serial number, voice identifier, radio frequency, or so forth. The wireless earpieces may be linked with the smart glasses and any number of other devices directly or through a network, such as a personal area network. In alternative embodiment, the wireless earpieces may be linked with the smart glasses utilizing wires with magnetic contacts. Any number of ports, connectors, and conductors may also be utilized to link the wireless earpieces with the smart glasses.

Next, the wireless earpieces receive user input through the wireless earpieces (step 304). The user input may represent voice or audio commands (e.g., words, clicks, noises, etc.), head gestures (e.g., tilting, jolts, nods, etc.), taps, touches, locations or positions, swipes, or motions. In one embodiment, the user may train the wireless earpieces two detects specific actions and associate those actions with commands or instructions that are executed or implemented by the wireless earpieces. The user input may be received utilizing any of the sensor systems of the wireless earpieces or wearable sensors in operative communication with the earpieces, such as microphones, touchscreens, accelerometers, gyroscopes, GPS chip, and so forth The wireless earpieces determine a command associated with the user input (step 306). As previously noted, the command may be associated with the user input by default or by customization efforts performed by the user. The command may represent an instruction, activity, or action performed by the wireless earpieces themselves or, alternatively, a command that is communicated to one or more external devices, such as the smart glasses. In one embodiment, the command may be associated with actions performed by the smart glasses.

Next, the wireless earpieces send the command to the smart glasses in communication with the wireless earpieces (step 308). In one embodiment, the command is immediately implemented by the smart glasses. In other embodiments, the command may be converted or translated into a command, instructions, or so forth that may be implemented by the smart glasses.

In some embodiments, where biometric information is collected with the wearable sensors, the command may be to display results of the biometric sensing. For example, where a plurality of wearable sensors at different locations include radar sensors used to collect pulse information which is communicated to the wireless earpieces for processing, the result of computations performed by the processor or other logic engine of the wireless earpieces may be received as input at the smart glasses.

At any time, the process of FIG. 4 may be terminated or suspended based on detected events. Suspension of communications may be performed to allow the user to focus on real world events applicable to the user. For example, the features of the illustrative embodiments may not be available to a user while driving.

FIG. 5 illustrates an example for improving biometric data by using a plurality of wearable devices which are networked or otherwise connected. Two wearable sensors 111 are shown each including a radar sensor 217A. The radar sensor 217A may be used to detect movements including those representing pulse or respiration or other physiological movements. The wearable sensors 111 may be placed at different locations on a body such as at different locations along an artery of the body. A first measurement may be made at one of the radar sensors 217A and a second measurement may be made at the other of the radar sensors 217A. These measurements may be processed at the respective wearable sensor 111 to some extent before being communicated to a processing device 500 which may be a processor or other intelligent control and may be located either in one of the wearable sensors 111 or in a separate device such as an earpiece. Based on these measurements and their respective timing, an arterial pulse wave transmit time may be determined. For example, the data from each of the measurements may be interpreted in order to generate a pulse wave form and the processing device may compare the timing of the pulse wave forms in order to determine a time differential there between corresponding to arterial pulse wave transmit time.

Information may be communicated between the wearable sensors 111 or between the wearable sensors 111 and the processing device 500 through wireless communication over a network, or otherwise including using the various communications methods previously described herein.

It is also to be understood that information from multiple wearable sensors may be combined to provide information not provided from a single sensor. Thus, for example, a waveform sensed at one location may be analyzed relative to a waveform sensed at another location in order to provide enhanced biometric monitoring or analysis. The example of arterial pulse wave transit time is merely one example. Other type of waveforms may be detected and analyzed relative to each other. It also to be understood that various types of sensors may be used. This may include radar sensors, lidar sensors, or other types of sensors described herein.

The illustrative embodiments provide a system, method, and network for augmenting the worldview of a user through a nonthreatening or privacy invading smart glass device. The information provided is safely done in such a way to prevent distraction of the user. As a result, the user may wirelessly distribute and view data and other information generated by devices of a personal area network. As a result, the data and information is available to the user in new and unparalleled manners. The smart glasses may also be utilized to enhance the vision of the user through magnification, dynamic lens adaptation, or vision correction.

The features, steps, and components of the illustrative embodiments may be combined in any number of ways and are not limited specifically to those described. In particular, the illustrative embodiments contemplate numerous variations in the smart devices and communications described. The foregoing description has been presented for purposes of illustration and description. It is not intended to be an exhaustive list or limit any of the disclosure to the precise forms disclosed. It is contemplated that other alternatives or exemplary aspects are considered included in the disclosure. The description is merely examples of embodiments, processes or methods of the invention. It is understood that any other modifications, substitutions, and/or additions may be made, which are within the intended spirit and scope of the disclosure. For the foregoing, it can be seen that the disclosure accomplishes at least all of the intended objectives.

The previous detailed description is of a small number of embodiments for implementing the invention and is not intended to be limiting in scope. The following claims set forth a number of the embodiments of the invention disclosed with greater particularity.

What is claimed is:

1. A method for improving biometric data by using a plurality of wearable devices on a wireless network, comprising:
    making a first measurement at a first radar sensor operatively connected to a first wearable device of the plurality of wearable devices and positioned at a first location on a body of a user;
    making a second measurement at a second radar sensor operatively connected to a second wearable device of the plurality of wearable devices and positioned at a second location on the body of the user; and
    detecting an arterial pulse wave transmit time using the first measurement and the second measurement.

2. The method of claim 1 further comprising communicating the first measurement to a processing device.

3. The method of claim 2 further comprising communicating the second measurement to the processing device wherein the processing device uses the first measurement and the second measurement to detect the arterial pulse wave transmit time.

4. The method of claim 3 further comprising communicating the arterial pulse wave transmit time to another device.

5. The method of claim 3 further comprising communicating the arterial pulse wave transmit time to a glasses display.

6. The method of claim 1 wherein the first wearable device is a first wireless earpiece and the second wearable device is a second wireless earpiece.

7. A method for improving biometric data by using a plurality of wearable devices on a wireless network, comprising:
    making a first biometric measurement of a first waveform at a first radar sensor operatively connected to a first wearable device of the plurality of wearable devices and positioned at a first location on a body;
    making a second biometric measurement of a second waveform at a second radar sensor operatively connected to a second wearable device of the plurality of wearable devices and positioned at a second location on the body; and
    analyzing the first biometric measurement of the first waveform and the second biometric measurement of the second waveform at a processing device in order to determine a pulse wave velocity.

8. The method of claim 7 further comprising making a third biometric measurement of a third waveform at a lidar sensor positioned at a third location on the body.

9. The method of claim 8 further comprising analyzing the third biometric measurement of the third waveform at the processing device in order to determine the pulse wave velocity.

* * * * *